(12) United States Patent
Seykora et al.

(10) Patent No.: US 11,653,966 B2
(45) Date of Patent: May 23, 2023

(54) TARGETED TORQUE RELIEF FOR TORQUE-BASED INSTRUMENTS

(71) Applicant: Acumed LLC, Hillsboro, OR (US)

(72) Inventors: Andrew W. Seykora, Portland, OR (US); Steven P. Horst, Dayton, OR (US); Mark B. Sommers, Beaverton, OR (US); Scott F. Mastroianni, Forest Grove, OR (US); Gregory D. Hutton, Beaverton, OR (US); James G. Falkner, Jr., Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 154 days.

(21) Appl. No.: 16/993,949

(22) Filed: Aug. 14, 2020

(65) Prior Publication Data
US 2022/0047312 A1 Feb. 17, 2022

(51) Int. Cl.
*A61B 17/88* (2006.01)
*A61B 17/16* (2006.01)
*A61B 17/86* (2006.01)

(52) U.S. Cl.
CPC ...... *A61B 17/8875* (2013.01); *A61B 17/1631* (2013.01); *A61B 17/1633* (2013.01); *A61B 17/162* (2013.01); *A61B 17/8605* (2013.01)

(58) Field of Classification Search
CPC ............ A61B 17/8875; A61B 17/1631; A61B 17/1728; A61B 17/1633; A61B 17/7082;
(Continued)

(56) References Cited

U.S. PATENT DOCUMENTS

2008/0027561 A1 1/2008 Mitelberg et al.
2010/0251861 A1* 10/2010 Sixto, Jr. ............. B25B 23/1427
81/436
(Continued)

OTHER PUBLICATIONS

International Search Report corresponding to related International Patent Application No. PCT/US2021/045563 dated Nov. 16, 2021, 3 pages.
(Continued)

*Primary Examiner* — Marcela I. Shirsat
(74) *Attorney, Agent, or Firm* — K&L Gates LLP

(57) ABSTRACT

The present disclosure provides medical instruments and medical instrument components having targeted torsional failure. Such targeted torsional failure helps prevent a surgeon from applying excessive torque that may damage an implant or bone, and also helps avoid the problems and complications that arise when medical instruments break within patients during surgical procedures. To provide such targeted torsional failure, the disclosed medical instrument components include a breakaway section designed so that the component breaks at a desired amount of torque, at a desired location, and in a desired way. The provided medical instrument components may also include a sleeve to increase side-loading strength that may otherwise be reduced due to the breakaway section. The increased side-loading strength may help prevent accidental bending-type failures. The presently disclosed medical instrument component therefore provides targeted torsional failure without sacrificing side-loading strength.

20 Claims, 19 Drawing Sheets

(58) Field of Classification Search
CPC .......... A61B 17/8605; A61B 2090/031; A61B 2090/037; A61B 90/03
USPC ......................................................... 606/80
See application file for complete search history.

(56) References Cited

U.S. PATENT DOCUMENTS

| | | |
|---|---|---|
| 2012/0063863 A1 | 3/2012 | Campau |
| 2012/0197309 A1 | 8/2012 | Steele |
| 2016/0367303 A1* | 12/2016 | Mahajan ............ A61B 17/8605 |
| 2018/0153599 A1 | 6/2018 | Daly et al. |
| 2020/0060743 A1 | 2/2020 | Rohlfing et al. |
| 2020/0163700 A1 | 5/2020 | Faulhaber |

OTHER PUBLICATIONS

International Written Opinion corresponding to related International Patent Application No. PCT/US2021/045563 dated Nov. 16, 2021, 5 pages.

International Preliminary Report corresponding to related International Application No. PCT/US2021/045563 dated Feb. 23, 2023, 7 pages.

\* cited by examiner

TARGETED TORQUE RELIEF FOR TORQUE-BASED INSTRUMENTS

BACKGROUND

In many orthopedic procedures, a surgeon uses a driver to insert screws into plates, nails, or implants, or across a fracture or joint fusion. If a surgeon applies an excessive amount of torque to insert a screw, the surgeon may damage the drive interface, plate, implant, bone, etc. Moreover, if the torque applied by the surgeon to insert the screw exceeds the strength of the driver tip, the driver tip will break off and will typically remain in the head of the screw. This same sort of breakage may occur in other surgical instruments as well. For example, taps, drills, or reamers may experience varying amounts of torque that may cause a portion of these instruments to break off in bone. The broken off pieces of these surgical instruments create several challenges or problems. One such problem is that surgical time is increased, in some instances, because time must be taken to retrieve the broken off piece and/or a screw, and in other instances, because a procedure (e.g., inserting a screw) must be repeated in a different location.

Another challenge or problem is that in some cases, the broken off instrument piece may be difficult or impossible to retrieve, thus requiring a surgeon to either leave the broken off piece within the patient or increase the invasiveness of the procedure in order to retrieve the implant or broken instrument piece. For example, of particular significance is the insertion of screws percutaneously. In these cases, visibility of the screw/driver interface is not possible and is often buried under layers of soft tissue, which makes it difficult or impossible to retrieve a broken off driver tip. In another example, if a driver tip, drill, tap, or reamer breaks close to, flush, or within a bone, it may be difficult to locate or grasp the broken off instrument piece such that it can be removed from the bone. In the case of a reamer preparing a long bone canal for a nail, it is imperative that a broken off piece of the reamer is retrievable. If the reamer breaks within the bone canal, this creates a difficult problem to solve of getting the broken piece out of the bone.

Leaving a driver tip within a patient creates potential for galvanic corrosion if the driver tip remains in the head of a screw constructed of a different material. An inability to remove the driver tip also prevents a surgeon from removing the screw that the driver tip is within and may prevent the surgeon from removing the implant, plate, etc. that the screws are securing, should a situation arise in which either are necessary.

One way to help prevent over torqueing, and thus help prevent the above-described challenges or problems, is the use of a torque-limiting driver that limits an amount of maximum torque that can be applied to a screw at the driver tip. A torque-limiting driver may be calibrated to a safe level of maximum torque that will not damage a plate, implant, bone, etc. and will not cause a driver tip to break off. Torque-limiting drivers, however, are bulky and expensive which may limit their usefulness in certain instances and also increases the cost of surgical supplies.

Additionally, it is difficult to maintain a reliable calibration state of a torque-limiting driver throughout the device's lifetime. For example, proper maintenance of a torque-limiting driver may require re-calibration every three hundred turns or clicks, yet there is no convenient way to keep track of how many turns or clicks have been performed. Therefore, torque-limiting drivers may often not be calibrated properly. In some cases, this may lead a surgeon to inadvertently apply excessive torque when the surgeon believes, falsely, that the torque-limiting driver is providing the surgeon with protection. Accordingly, a driver tip may still break off while using a torque-limiting driver, presenting the problems or challenges described above. In addition, an incorrectly calibrated torque-limiting driver that leads a surgeon to inadvertently apply lower than desired torque has its own set of drawbacks. Such under-torqueing may result in screw prominence, screw backout, or insufficient fixation or reduction of the fracture, osteotomy, or fusion.

Another way to help a surgeon prevent applying excessive torque is a breakaway construct in which a driver and a screw are machined as a single component. The interface between the driver and the screw in such a construct is designed so that the driver may deliver the required torque necessary to implant the device, but also so that the interface facilitates breakage between the driver and the screw. For example, the interface may be constructed with a reduced side loading strength that facilitates breakage.

This type of breakaway construct, however, does not always break as designed and may require a surgeon to cut the driver apart from the screw. Conversely, in other instances, the driver may break away from the screw earlier than intended, such as from unintended side loading. The breakaway construct also requires a driver and screw to be machined as one piece, which results in only a one-time use and additionally limits flexibility with respect to a driver and/or screw that may be used for a procedure. Further, the screw in such a construct may not have a drive mechanism after the driver breaks away such that it may be removed in the future. Additionally, this breakaway construct does not solve the problems or challenges regarding non-driver surgical tools.

Accordingly, a need exists for a mechanism that controls how and where a shaft under torque breaks in order to solve the above-described problems and challenges.

SUMMARY

The present disclosure provides new and innovative medical instrument components that ensure torque failure of the components occurs at a desired amount of torque, at a desired location, and in a desired way. This helps prevent over-torqueing and eliminate the problems and challenges that may arise when a medical instrument fails during a surgical procedure. In an example, a medical instrument component includes an elongated shaft and a sleeve. The elongated shaft has a first portion between a second portion and a third portion. The elongated shaft's first portion is configured to have a lower torsional strength than the second and third portions such that the first portion experiences torsional failure at a lower torque force than the second or third portions. The sleeve is positioned around the elongated shaft's first portion and is connected to either the elongated shaft's second or third portion.

The sleeve provides additional side-load strength to the elongated shaft's first portion to prevent accidental bending-type breakage. For instance, the configuration of the elongated shaft's first portion to have a reduced torsional strength may also reduce the first portion's side-load strength. Therefore, the sleeve helps the elongated shaft maintain its side-loading strength without any impact to the first portion's reduced torsional strength. The sleeve may also help contain any broken fragments after the elongated shaft fails at its first portion.

BRIEF DESCRIPTION OF THE DRAWINGS

FIGS. 1A to 1K illustrate example medical instrument components having a breakaway portion with a lowered torsional strength, according to an aspect of the present disclosure.

DETAILED DESCRIPTION

Figure 1A:
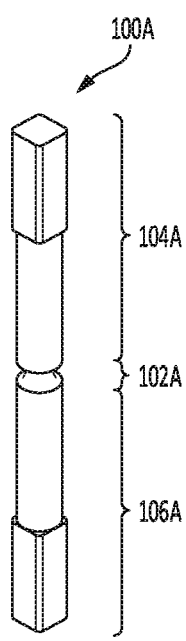

The presently disclosed medical instruments and medical instrument components provide medical instruments with targeted torsional failure. For instance, the disclosed medical instrument component may be a driver shaft that may be fixed or coupled to a handle for driving a screw. In other instances, the disclosed medical instrument component may be a reamer shaft or drill shaft. In other instances still, the disclosed medical instrument component could be a portion of a medical instrument other than a shaft. Such targeted torsional failure helps prevent a surgeon from applying excessive torque that may damage an implant, instrument, or bone. The targeted torsional failure also helps avoid the problems and complications that arise when medical instruments or implants break within patients during surgical procedures.

To provide such targeted torsional failure, the disclosed medical instrument components include a breakaway section that helps facilitate torsional failure occurring only at the breakaway section and at a particular amount of applied torque. Stated differently, a medical instrument component's breakaway section is designed so that the component breaks at a desired amount of torque, at a desired location, and in a desired way. For example, a medical instrument component's breakaway section may be constructed to fail upon application of an amount of torque below a critical amount of torque that may cause damage to an implant or bone. Accordingly, the medical instrument component fails prior to a surgeon applying the critical amount of torque, and helps prevent damage. Additionally, because the torque limiting factor of the provided medical instrument component is a construction of the component's material, the medical instrument component does not need to be calibrated like typical torque-limiting drivers, and therefore eliminates the maintenance issues of typical torque-limiting drivers that may cause accidentally and unknowingly applying excessive or inadequate torque.

In another example, the medical instrument component includes an elongated shaft and the breakaway section may be positioned on a portion of the elongated shaft that is not inserted within a patient during a procedure. This helps ensure that if the medical instrument component fails, it fails outside of the patient, thus making it easier for the surgeon to quickly retrieve the broken off piece because it can be grabbed external to the patient. Unpredictability of where a medical instrument may fail, and therefore unpredictability of potential procedural complications due to broken instrument pieces, may accordingly be limited.

In addition, the breakaway section's construction to reduce the section's torsional strength may also reduce the section's side-loading strength. The reduced side-loading strength may cause accidental bending-type failures as a surgeon uses an instrument of which the medical instrument component is a part. Accordingly, to help prevent such accidental bending-type failures, the provided medical instrument component may include a sleeve positioned around the breakaway section. The sleeve may be fixed in position around the breakaway section or its position may be adjustable such that the breakaway section's torsional strength and bending strength is adjustable. The presently disclosed medical instrument component therefore provides targeted torsional failure without sacrificing side-loading strength. The sleeve may also help contain material fragments that may break free upon the medical instrument component failing at the breakaway section.

FIGS. 1A to 1J illustrate example medical instrument components that have a breakaway section with a lowered torsional strength as compared to the rest of the component. The various illustrated breakaway section configurations may require differing amounts of torque for failure. Accordingly, in some aspects of the present disclosure, a particular breakaway section configuration may be selected based on the surgical procedure it will be used for. Additionally, it should be appreciated that the example medical instrument components illustrated in FIGS. 1A to 1J are illustrated in a manner solely to show the respective example breakaway sections. In various instances, the second or third portions of the example medical instrument components may be constructed as or to include a drive feature (e.g., a screwdriver tip), a coupling or connecting feature (e.g., FIG. 6A, 6B, or 10), a screw (e.g., FIGS. 8A to 8C and 9A to 9C), a cutting portion of a drill bit, a reaming portion of a reamer, an implant (e.g., FIGS. 11A and 11B), a drilling guide (FIGS. 11A and 11B), etc.

In some examples, a provided medical instrument component may have a cross sectional area that continuously and uniformly decreases within the breakaway section to a minimum cross sectional area. FIG. 1A illustrates an example medical instrument component 100A having an elongated shaft with a first portion 102A, a second portion 104A, and a third portion 106A. As illustrated, the cross sectional area of the medical instrument component 100A in its first portion 102A (e.g., the breakaway section) continuously and uniformly decreases from a cross sectional area at the second and third portions 104A, 106A to a minimum cross sectional area. In some instances, such as the illustrated example, the cross sectional area decreases continuously in a concave manner.

Figure 1B:
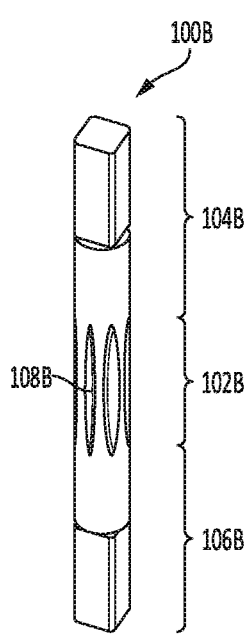
Figure 1C:
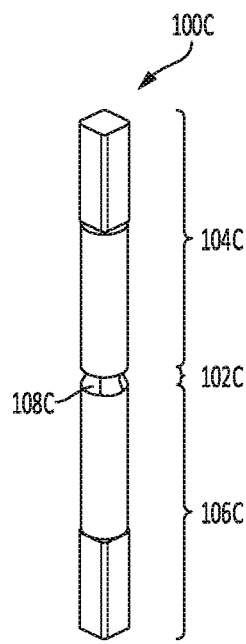
Figure 1D:
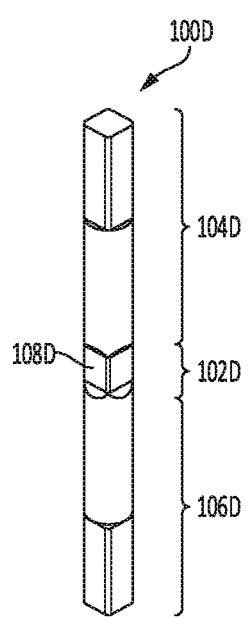
Figure 1E:
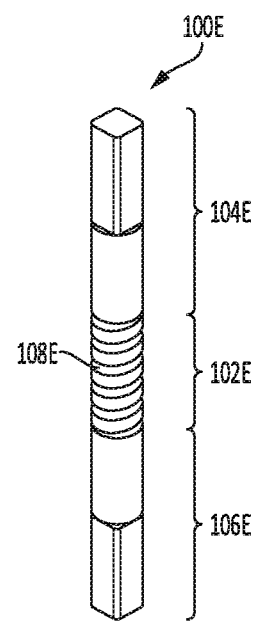
Figure 1F:
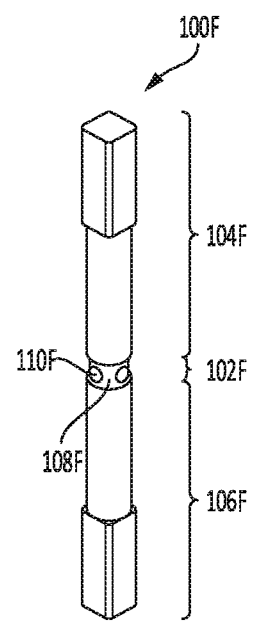

In other instances, the cross sectional area may decrease linearly from the second and third portions 104A, 104B. For example, FIG. 1K illustrates an example medical instrument component 100K having an elongated shaft with a first portion 102K, a second portion 104K, and a third portion 106K. A cross sectional area of the second portion 104K and the third portion 106K decrease linearly to a minimum cross sectional area 116K within the first potion 102K (e.g., breakaway portion). In some instances, the minimum cross sectional area 116K may continue for a segment of the first portion 102K, such as the illustrated example.

In other examples, the provided medical instrument component may include multiple indentations within its breakaway section. FIG. 1B illustrates an example medical instrument component 100B having an elongated shaft with a first portion 102B, a second portion 104B, and a third portion 106B. As illustrated, the first portion 102B includes multiple elongated indentations 108B, though only one is indicated for the sake of clarity. FIG. 1C illustrates an example medical instrument component 100C having an elongated shaft with a first portion 102C, a second portion 104C, and a third portion 106C. As illustrated, the first portion 102C includes multiple concave, sphere-like indentations 108C, though only one is indicated for the sake of clarity. FIG. 1D illustrates an example medical instrument component 100D having an elongated shaft with a first portion 102D, a second portion 104D, and a third portion 106D. As illustrated, the first portion 102D includes multiple (e.g., four) indentations 108D having a flat surface, though only one is indicated for the sake of clarity. In this example, the multiple indentations 108D form a square perimeter, though in other examples, there may be more or less flat surface indentations 108D that form other perimeter shapes.

In at least one example, the provided medical instrument component may include a single, continuous indentation within its breakaway section. FIG. 1E illustrates an example medical instrument component 100E having an elongated shaft with a first portion 102E, a second portion 104E, and a third portion 106E. As illustrated, the first portion 102E includes a single, continuous spiral indentation 108E.

In some aspects, the provided medical instrument component may include multiple indentations of differing depths within its breakaway section. FIG. 1F illustrates an example medical instrument component 100F having an elongated shaft with a first portion 102F, a second portion 104F, and a third portion 106F. The first portion 102F includes a first indentation 108F that extends around the perimeter of the medical instrument component 100F. The first portion 102F also includes multiple indentations 110F that have a greater indentation depth than the indentation 108F. Only one indentation 110F is indicated for the sake of clarity.

Figure 1G:
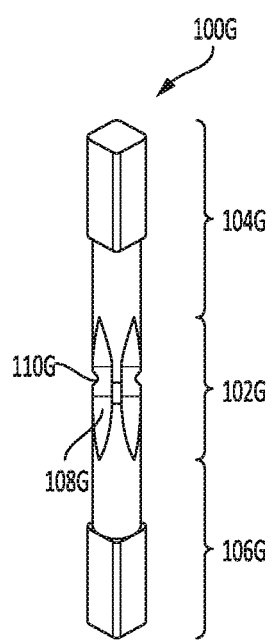

FIG. 1G illustrates an example medical instrument component 100G having an elongated shaft with a first portion 102G, a second portion 104G, and a third portion 106G. The first portion 102G includes multiple indentations 108G, though only one indentation 108G is indicated for the sake of clarity. Between each of the indentations 108G, the first portion 102G also includes an indentation 110G, though only one indentation 110G is indicated for the sake of clarity. The indentations 108G have a greater indentation depth than the indentations 110G.

Figure 1H:
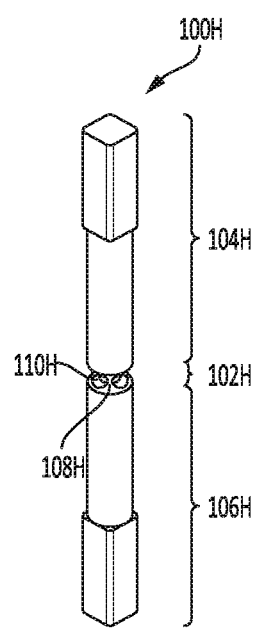

In some aspects, the provided medical instrument component may include one or more openings that extend through the elongated shaft within its breakaway section. FIG. 1H illustrates an example medical instrument component 100H having an elongated shaft with a first portion 102H, a second portion 104H, and a third portion 106H. The first portion 102H includes an indentation 108H that extends around the perimeter of the medical instrument component 100H. The first portion 102H also includes multiple through-holes 110H that extend from one side of the elongated shaft to the other. Only one through-hole 110H is indicated for the sake of clarity.

Figure 1J:
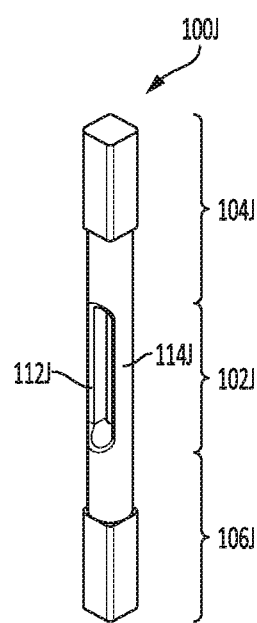
Figure 1K:
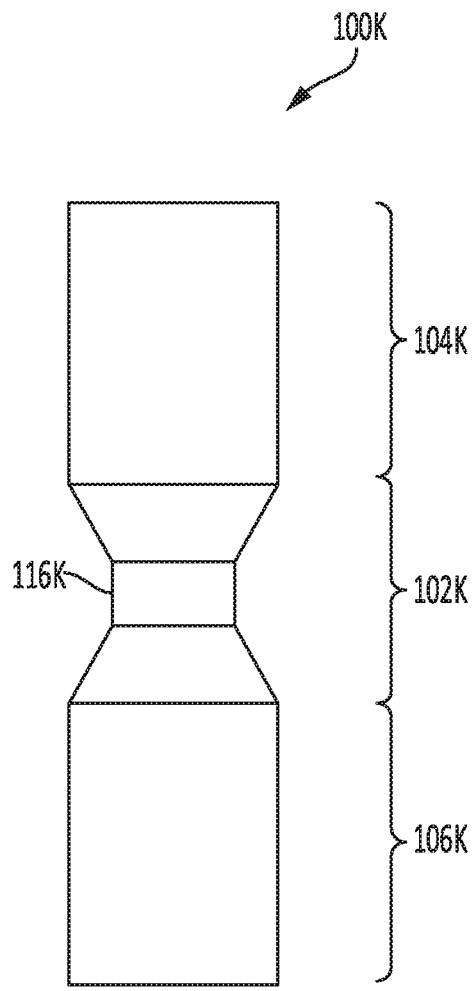

FIG. 1J illustrates an example medical instrument component 100J having an elongated shaft with a first portion 102J, a second portion 104J, and a third portion 106J. As illustrated, the medical instrument component 100J includes an elongated opening 116J through its elongated shaft such that the first portion 102J includes elongated arms 112J and 114J. In other examples, the opening 116J may be smaller such that the arms 112J and 114J are not elongated. The opening 116J may alternatively be larger. Additionally, in the illustrated example, the opening 116J through the elongated shaft of the medical instrument component 100J is symmetrical. In other instances, the opening 116J may be asymmetrical such that one end of the opening is larger than its opposite end. In contrast to the example medical instrument components illustrated in FIGS. 1A to 1H which may fail via breakage (e.g., a ductile or brittle failure mode), the example medical instrument component 100J may fail via plastic deformation.

Figure 7:
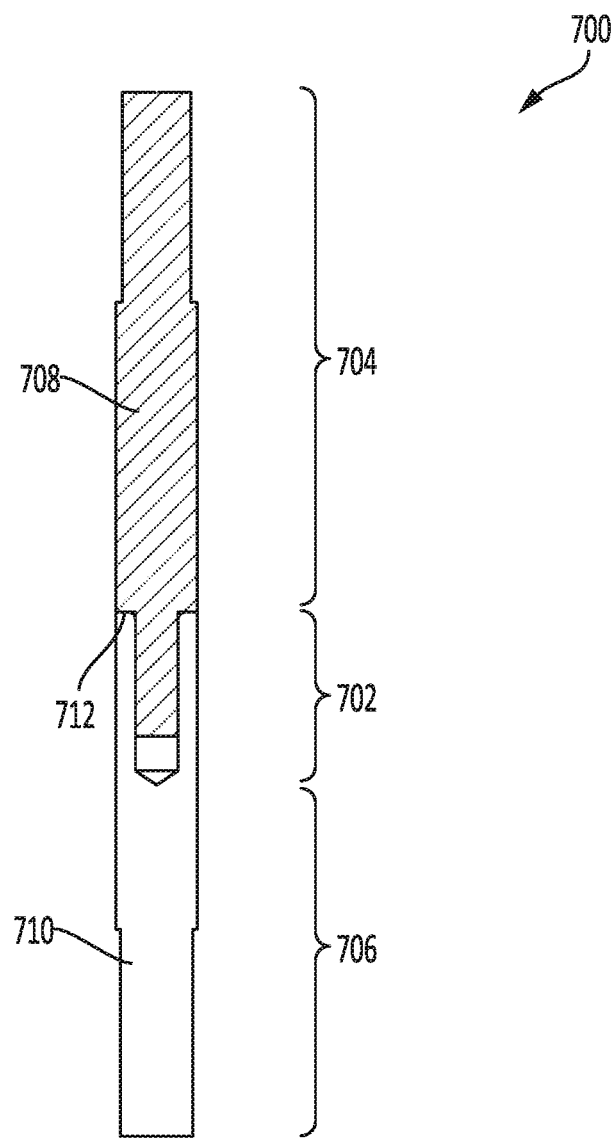
FIG. 7 illustrates a medical instrument component having two portions slip fit and welded together, according to an aspect of the present disclosure.

In some aspects of the present disclosure, the provided medical instrument component may include two separate parts that are slip fit together and welded to form a breakaway section. FIG. 7 illustrates an example medical instrument component 700 having a part 708 slip fit within a part 710. The part 708 is welded to the part 710 at the weld 712. The elongated shaft of the medical instrument component 700 includes a first portion 702 (e.g., breakaway section), a second portion 704, and a third portion 706. The weld 712 may be controlled such that it is designed to break or fail at a specific, critical amount of torque. This weld control can be achieved by manipulating weld parameters such as weld size, voltage, and number of welds.

In some aspects of the present disclosure, the provided medical instrument component may be heat-treated (e.g., induction hardening). For instance, as is evident by the above-illustrated breakaway section examples, a reduction of material in the breakaway section as compared to the rest of the medical instrument component's elongated shaft may contribute to the reduction in the breakaway section's torsional strength. Additionally or alternatively, the medical instrument component may be heat-treated to generate or contribute to the breakaway section's reduced torsional strength. The heat treatment parameters may be adjusted to target a desired torque strength or desired failure mode for the breakaway section or other portions of the elongated shaft. For example, a brittle failure typically results in sharp edges and potentially debris, whereas a ductile failure typically leaves a smooth surface with no debris.

The medical instrument component may be uniformly heat-treated across the elongated shaft or certain portions of the elongated shaft may be heat-treated differently than other portions. For instance, the second and/or third portions may be heat-treated to increase their hardness, while the first portion (e.g., the breakaway section) is not hardened. Such instances may help ensure adequate strength for the second and/or third portions, which may include a drive interface or drill or reamer cutting flutes, while ensuring a ductile failure mode for the breakaway section. A breakaway section that is in an annealled state has a greater ellongation and will have a large angle of deformation prior to failure.

In at least one example, the weld configuration of medical instrument component 700 can make it easier to heat-treat one portion of the elongated shaft of the medical instrument component 700 while another portion remains annealed because the parts 708 and 710 are separate prior to being welded together. In some aspects, the weld 712 may be controlled such that it is not intended to break, but rather is utilized to join a heat-treated part with a non-heat-treated part. For example, the part 710 may be heat-treated and include a driver tip, whereas the part 708 may remain annealed and include a breakaway section.

The breakaway sections illustrated in FIGS. 1A to 1J and FIG. 7 are intended merely as exemplary. The breakaway section of a provided medical instrument component may have suitable configurations other than those illustrated that similarly provide a reduced torsional strength for the breakaway section. For instance, a medical instrument component may include any suitable combination of features of the various examples described FIGS. 1A to 1J and FIG. 7. In an example, a medical instrument component may include the flat surface indentations of FIG. 1D and the through-holes of FIG. 1G.

Figure 2:
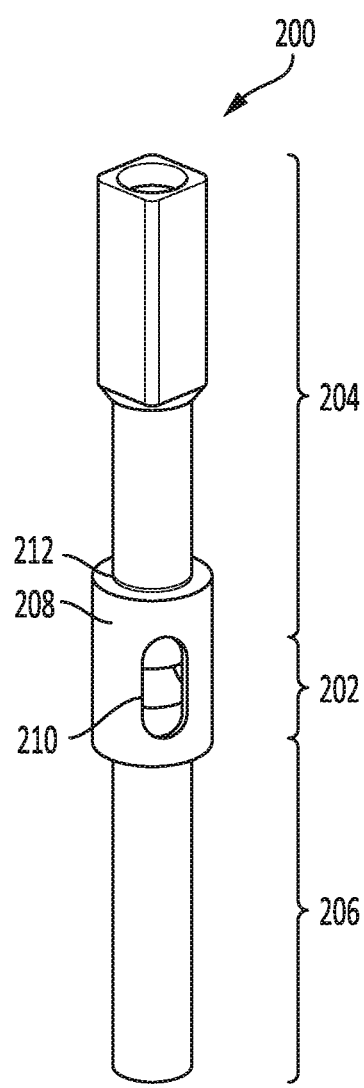
FIG. 2 illustrates a medical instrument component having a fixed sleeve, according to an aspect of the present disclosure.

As described above, in some instances the provided medical instrument component may include a sleeve to increase side-loading strength at the breakaway section that may otherwise have a reduced side-loading strength. FIG. 2 illustrates an example medical instrument component 200 having a sleeve 208. The medical instrument component 200 has an elongated shaft including a first portion 202 (e.g., a breakaway section), a second portion 204, and a third portion 206. As with the example medical instrument components illustrated in FIGS. 1A to 1J, it should be appreciated that the example medical instrument component 200 is illustrated in a manner solely to show the breakaway section (the first portion 202) and the sleeve 208. In various instances, the second portion 204 or the third portion 206 may be constructed with a drive feature, a coupling or connecting feature, a cutting portion of a drill bit, a reaming portion of a reamer, etc.

The sleeve 208 is positioned around the first portion 202 and a section each of the second portion 204 and the third portion 206. The extension of the sleeve 208 into the second portion 204 and the third portion 206 helps take side-loading stress away from the breakaway section and places it on the sleeve 208 instead to increase the side-loading strength at the first portion 202. The sleeve 208 may include an opening 210 in some instances so that a surgeon can see the first portion 202, for example, to see if there are indications of an impending failure. In the illustrated example, the sleeve 208 is connected to the second portion 204 of the elongated shaft. In other examples, the sleeve 208 may alternatively be connected to the third portion 206. Connecting the sleeve 208 to only the second portion 204 or the third portion 206 enables the same amount of torque to be applied to the first portion 202 as compared to a medical instrument component without a sleeve. Additionally, the sleeve 208 is illustrated as fixedly connected to the second portion 204 such that its positioning is fixed in place. For example, the sleeve 208 may be welded to the second portion 204 at the weld 212.

Figure 3A:
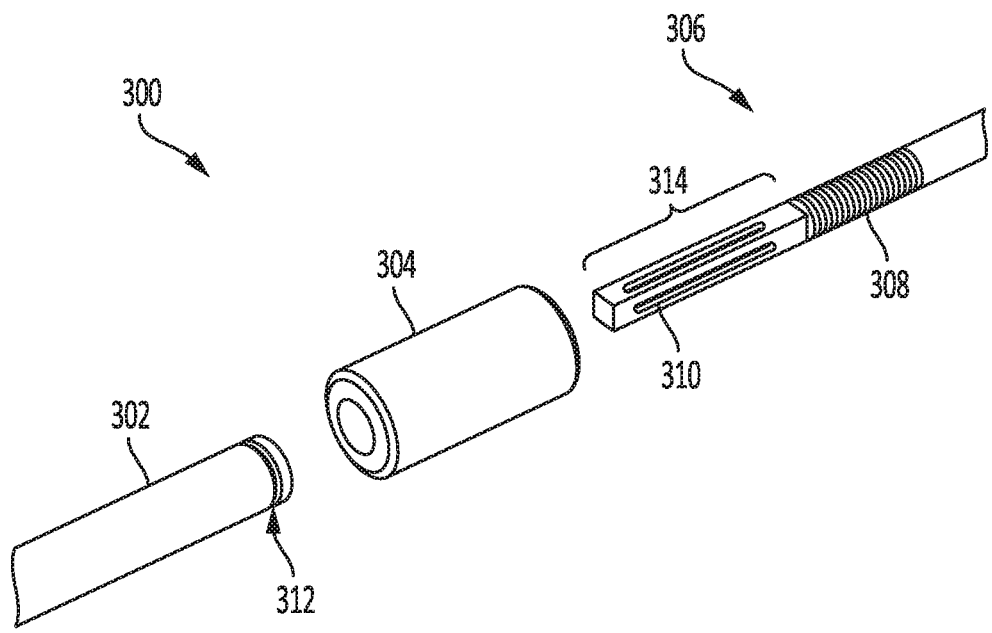
FIG. 3A illustrates an exploded perspective view of an example medical instrument component with an adjustable sleeve, according to an aspect of the present disclosure.
Figure 3B:
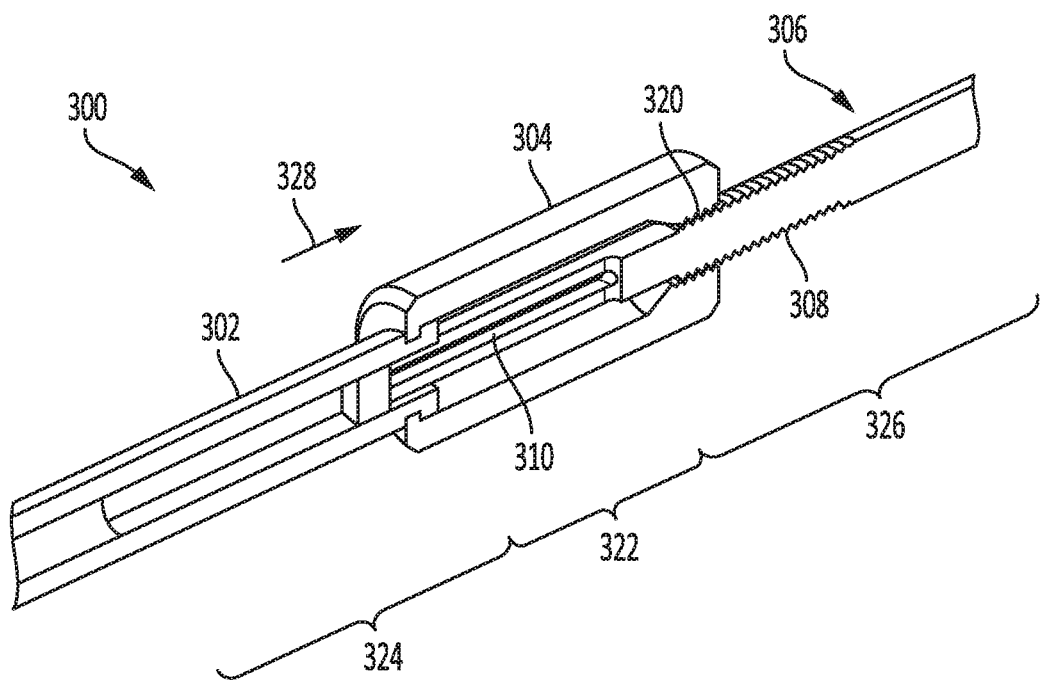
FIG. 3B illustrates a cross sectional view of the example medical instrument component of FIG. 3A, according to an aspect of the present disclosure.

In other examples, the provided medical instrument component may include a sleeve with an adjustable positioning. The positioning of the sleeve may adjust the medical instrument component's critical torsional strength (e.g., the torque required to cause the breakaway section to fail). FIGS. 3A and 3B illustrate an exploded perspective view and a cross sectional view, respectively, on an example medical instrument component 300 with an adjustable sleeve 304. The medical instrument component 300 includes a shaft 302, the sleeve 304, and a shaft 306. At least a portion of the shaft 302 is hollow with a non-circular channel such that at least a portion of the shaft 306 may be positioned within the shaft 302. The shaft 302 may include a notch 312 such that the shaft 302 may be coupled to the sleeve 304 as illustrated in FIG. 3B.

In some instances, the sleeve 304 may include interior threading 320. In such instances, the shaft 306 includes a threaded portion 308. The threaded portion 308 is configured to engage with the interior threading 320 such that a surgeon may adjust the positioning of the sleeve 304 along the threaded portion 308. In other instances, a positioning of the sleeve 304 along the shaft 306 may be adjusted via friction instead of threaded engagement. For example, the interior of the sleeve 304 may include at least one flexible concave shaped portion that applies inward force towards the shaft 306. The inward force is sufficient to maintain a positioning of the sleeve 304 while also enabling a surgeon to slide the sleeve 304 along the shaft 306.

At least a segment of the shaft 306 has a non-circular cross sectional area capable of transmitting torque. For instance, the segment 314 of the shaft 306 has a square cross sectional area. The shaft 306 includes one or more elongated openings 310 along the segment 314. The one or more elongated openings 310 decrease the torsional strength of the shaft 306 in the segment 314 as compared to other segments of the shaft 306 since material is removed. Accordingly, at least a portion of the segment 314 is a torque limiting factor as described below. When a critical torque is reached the torque limiting factor portion of the segment 314 of the shaft 306 may fail by plastic deformation. Larger openings corresponds to decreased torsional strength.

The proportion of the one or more openings 310 that is positioned within the shaft 302 determines a torque strength of the medical instrument component 300. Torque exerted on a section of the shaft 306 positioned within the shaft 302 is transferred to the shaft 302. The section of the segment 314 that remains within the sleeve 304 is then the torque-limiting factor. A surgeon may therefore increase the torque strength of the medical instrument component 300 may advancing the positioning of the sleeve 304 along the shaft 306 in the direction the arrow 328. The surgeon may decrease the torque strength by advancing the positioning of the sleeve 304 in the opposite direction. In this way, the medical instrument component 300 may be described as having a first portion 322, a second portion 324, and a third portion 326. The first portion 322 is the portion of the segment 314 that remains within the sleeve 304, as indicated, since it is the torque-limiting factor. The second portion 324 is the shaft 302 and any portion of the shaft 306 that is within the shaft 302. The third portion 326 is the remaining portion of the shaft 306.

Figure 4:
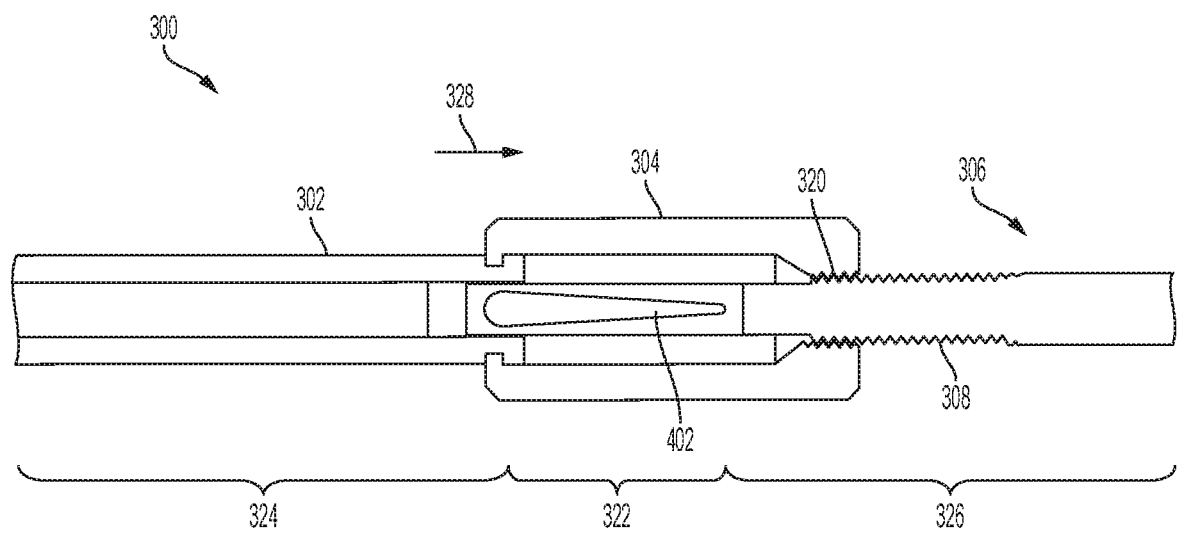
FIG. 4 illustrates a cross sectional view of the example medical instrument component of FIGS. 3A and 3B having an asymmetrical opening, according to an aspect of the present disclosure.

In some instances, a shape of the one or more openings 310 contributes to the torque strength of the medical instrument component 300. FIG. 4 illustrates a cross section of the example medical instrument component 300 having an asymmetrical opening. For instance, the example asymmetric opening 402 is larger on its end nearest the shaft 302 as compared to its opposite end. A larger opening corresponds to a lower torque strength. Therefore, as the sleeve 304 is advanced in the direction of the arrow 328, the torque of the medical instrument component 300 is increased not only because of the description in connection with FIG. 3B, but also because the size of the asymmetric opening 402 remaining within the sleeve 304 reduces. As such, the torque strength of the medical instrument component 300 may increase or decrease more rapidly in response to a change in the positioning of the sleeve 304 when having one or more asymmetric openings as compared to having one or more symmetric openings. In some instances, the medical instrument component 300 may have one or more symmetric openings and one or more asymmetric openings.

Figure 5A:
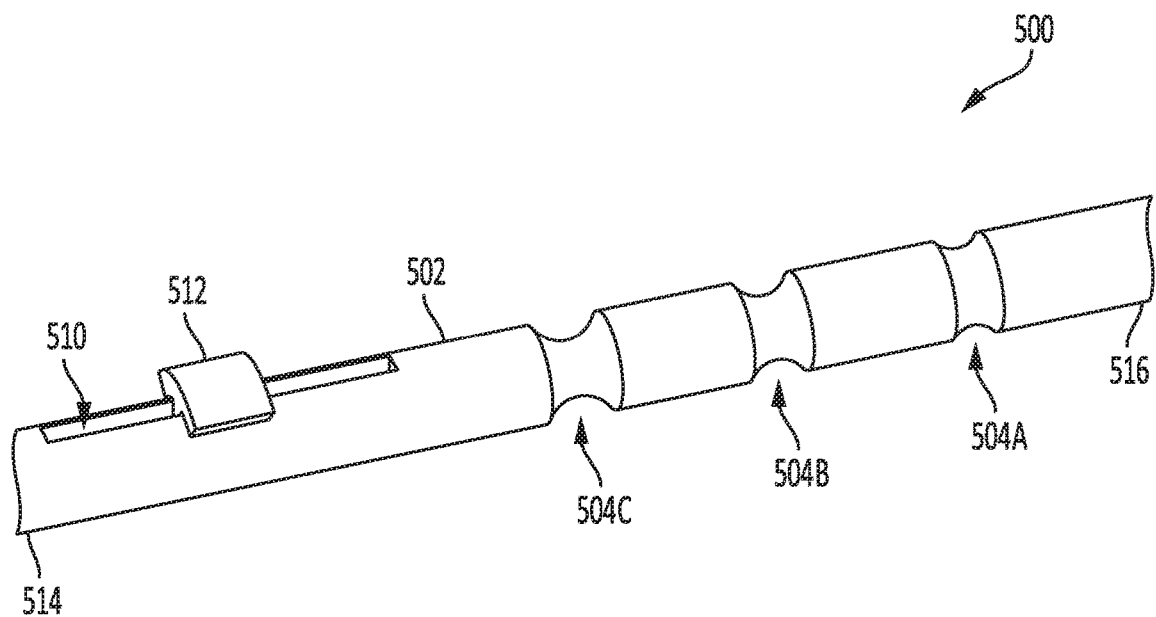
FIGS. 5A and 5B illustrate a perspective and cross sectional view, respectively, of a medical instrument component with three zones to adjust the component's torque strength, according to an aspect of the present disclosure.
Figure 5B:
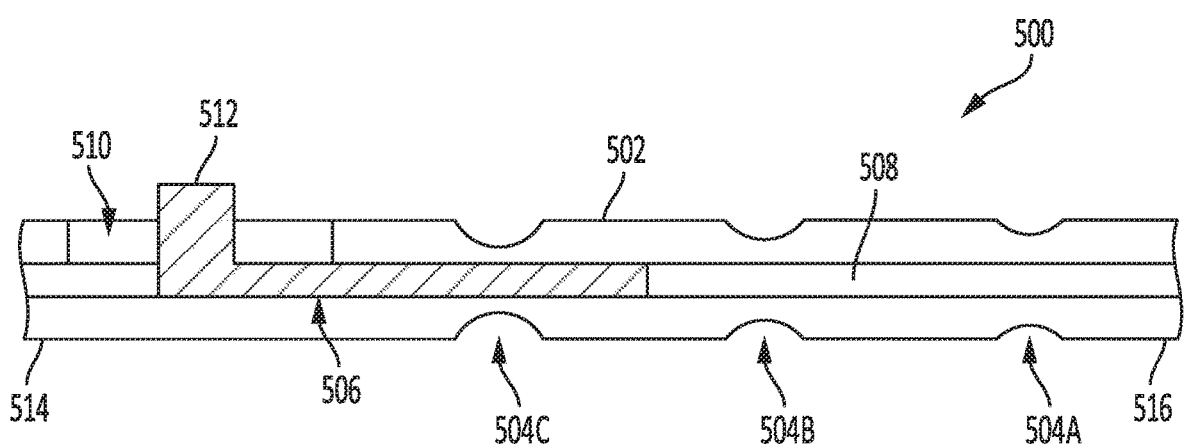

FIGS. 5A and 5B illustrate a perspective and cross sectional view, respectively, of another example of a medical instrument component with an adjustable torque strength. The example medical instrument component 500 includes an elongated shaft 502 having three separate breakaway sections 504A, 504B, 504C that each help provide a different torque strength for the medical instrument component 500. In various examples, a distal end 516 of the shaft 502 may include a driver or cutting flutes while the proximal end 514 of the shaft 502 may include a driver connector, or vice versa. Each of the breakaway sections 504A, 504B, 504C may be concave indentations, as illustrated. The torsional strength of the breakaway section 504C is the lowest because its indentation is the greatest, and thus its cross sectional area is the smallest. Accordingly, the breakaway section 504A has the greatest torsional strength and the torsional strength of the breakaway section 504B is in the middle. Alternatively, the breakaway sections 504A, 504B, 504C may be constructed as one of the breakaway sections described in connection with FIGS. 1A to 1J.

The elongated shaft 502 also includes a channel 508 within its interior. A non-circular rod 506 is inserted within the channel 508. For example, the non-circular rod 506 may have a square or hexagonal cross-section or other suitable non-circular cross-section that can transmit torque. The positioning of the non-circular rod 506 is adjustable within the channel 508. For example, the non-circular rod 506 may include an adjustment tab 512 that extends to exterior of the elongated shaft 502 through a slot 510 in the elongated shaft 502. A surgeon may move the adjustment tab 512 to adjust the positioning of the non-circular rod 506 within the channel 508. The medical instrument component 500 may also be configured such that the non-circular rod 506 maintains its positioning within the channel 508 when it is not being adjusted. For instance, friction between the adjustment tab 512 and the elongated shaft 502 may maintain the positioning of the non-circular rod 506 in some examples.

The positioning of the non-circular rod 506 is adjustable in order to adjust the torque strength of the medical instrument component 500. More specifically, when the non-circular rod 506 is within the channel 508 towards the proximal end 514 and prior to reaching the breakaway section 504C, the breakaway section 504C is active. Stated differently, the medical instrument component 500 has the torsional strength of the breakaway section 504C. As the non-circular rod 506 is translated past the breakaway section 504C, but prior to reaching the breakaway section 504B (e.g., as illustrated in FIG. 5), the breakaway section 504B is active. Stated differently, as torque is applied to the medical instrument component 500 in this orientation, torque is transferred into the non-circular rod 506 at the breakaway section 504C, leaving the breakaway section 504B as the limiting factor having the lowest torque strength. The medical instrument component 500 therefore has the torsional strength of the breakaway section 504B.

As the non-circular rod 506 is translated past the breakaway section 504B, but prior to reaching the breakaway section 504A, the breakaway section 504A is active. The medical instrument component 500 therefore has the torsional strength of the breakaway section 504A. As the non-circular rod 506 is translated past the breakaway section 504A, the medical instrument component 500 has the torsional strength of the elongated shaft 502 since the torque at each breakaway section 504A, 504B, 504C is transferred into the non-circular rod 506. Accordingly, the positioning of a first portion (e.g., the breakaway section), a second portion, and a third portion as used herein of the example medical instrument component 500 is adjustable along the elongated shaft 502. For instance, the first portion of the medical instrument component 500 may be either the breakaway section 504A, 504B, or 504C depending on which is active as described above.

The dimensions of the medical instrument component 500 may vary between different examples of the present disclosure, such as the spacing between breakaway sections 504A, 504B, and/or 504C or the length of the non-circular rod 506. It should be appreciated that the dimensions illustrated in FIGS. 5A and 5B (and all other figures included herein) are merely illustrative. The non-circular rod 506 may have a length such that it may pass through only the breakaway sections 504B and 504C, or may have a length such that it may pass through each of the breakaway sections 504A, 504B, and 504C.

Figure 6A:
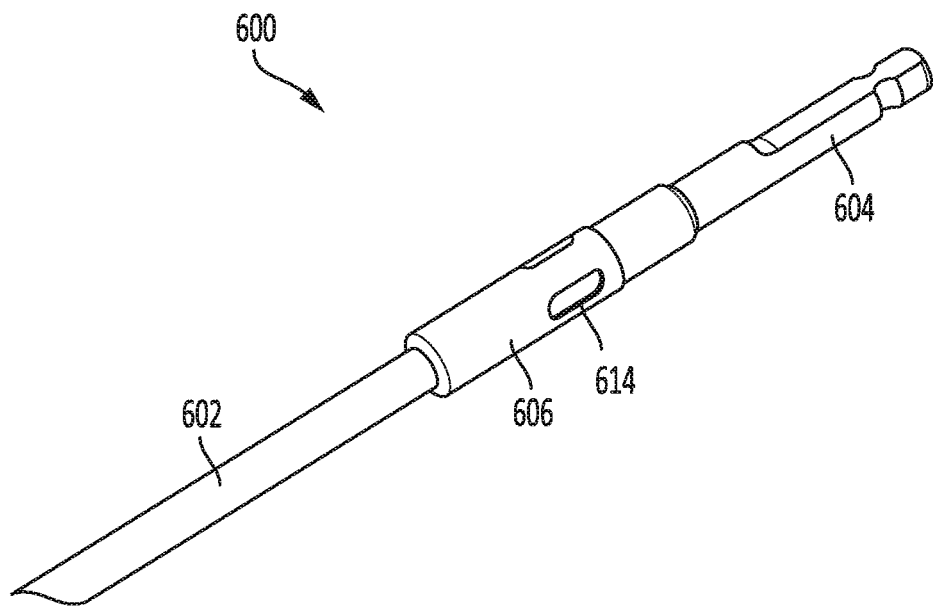
FIGS. 6A and 6B illustrate a medical instrument component that may be used as a driving mechanism after breakage, according to an aspect of the present disclosure.
Figure 6B:
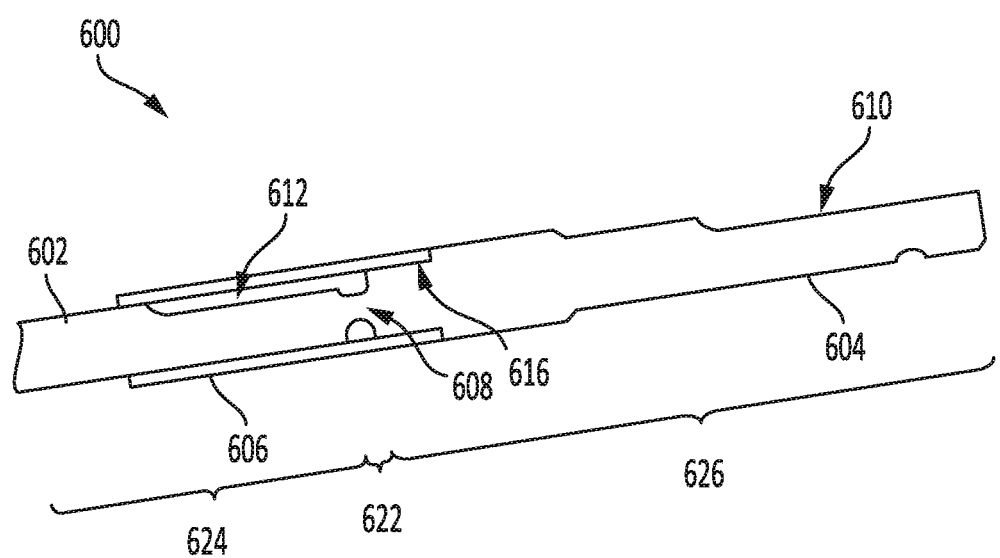

In some aspects of the present disclosure, the elongated shaft of the provided medical instrument component may be constructed such that a desirable configuration of the elongated shaft is obtained after breakage. For instance, the elongated shaft may be constructed such that a surgeon may continue to use the medical instrument component after breakage. FIGS. 6A and 6B illustrate a perspective and cross sectional view, respectively, of an example medical instrument component 600 that may continue to be attached to a driver after breakage. The medical instrument component 600 includes an elongated shaft 602 having a first portion 622, second portion 624, and third portion 626. The first portion 622 includes a breakaway section 608. The breakaway section 608 may be configured, for example, according to any of the breakaway sections described in connection with FIGS. 1A to 1J and FIG. 7.

A sleeve 606 is positioned around the breakaway section 608. In some instances, the sleeve 606 may have one or more openings 614 (e.g., the opening 210). The one or more openings 614 enable a surgeon to see the breakaway section 608, for instance, to see if there are indications of an impending failure. The openings 614 may also enable cleaning and sterilization procedures to be performed within the sleeve 606. In various instances, the sleeve 606 may be attached to either the second portion 624 or the third portion 626. For example, the sleeve 606 may be attached to the third portion at the weld 616.

The third portion 626 is constructed to include a drive connector 604. In this example, the driver connector 604 is an AO drive feature constructed so that the medical instrument component 600 may be attached to a driver. In other examples, the driver connector 604 may be constructed for attachment to drivers having a different drive feature. The second portion 624 of the elongated shaft 602 adjacent to the breakaway section 608 is configured to at least substantially match the driver connector 604. For instance, the driver connector 604 includes a notch 610, which enables the driver connector 604 to attach to a driver. The second portion 624 of the elongated shaft 602 also includes a notch 612 that is the same or similar to the notch 610. In this way, after the medical instrument component 600 fails or breaks at the breakaway section 608, a surgeon can still attach the remaining portion of the medical instrument component 600 to the driver for additional tightening or removal of a securement component (e.g., a screw).

In instances in which the sleeve 606 is attached to the third portion 626, the driver connector 604 and the sleeve 606 are both detached from the elongated shaft 602 upon failure at the breakaway section 608. In other instances, the sleeve 606 may be attached to the second portion 624 so that it remains attached to the second portion 624 after breakage. In such instances, the sleeve 606 may be removable from the second portion 624 so that the remaining portion may be attached to a driver.

Figure 8A:
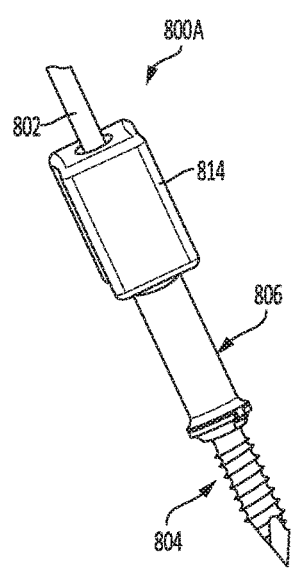
FIGS. 8A and 8B illustrate a non-keyed snap-off screw instrument having an adjustable sleeve, according to an aspect of the present disclosure.
Figure 8B:
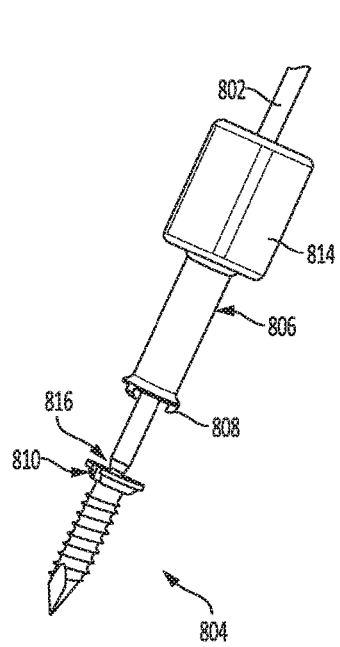

In some aspects of the present disclosure, the provided medical instrument component may be, or may be a component of, a non-keyed or keyed snap-off screw instrument. FIGS. 8A and 8B illustrate an example medical instrument component 800A of a non-keyed snap-off screw instrument. The medical instrument component 800A includes an elongated shaft 802 (e.g., a second portion) connected to a screw 804 (e.g., a third portion). The elongated shaft 802 may be connected to a handle or other suitable configurations of a snap-off screw instrument. The medical instrument component 800A is constructed to include a breakaway section 816 (e.g., a first portion) at the interface between the screw 804 and the elongated shaft 802. The breakaway section enables the screw 804 to break from the elongated shaft 802 upon a critical torque or side-load being applied. For instance, a surgeon may "snap" the elongated shaft 802 off the screw 804 by bending the elongated shaft 802 to the side after the screw 804 is inserted. In one example, the breakaway section 816 may be constructed as a decrease in cross sectional area of the elongated shaft (e.g., the breakaway section 912 in FIG. 9). In other examples, the breakaway section 816 may be constructed as one of the breakaways sections illustrated in FIGS. 1A to 1J or FIG. 7.

The example medical instrument component 800A also includes an adjustable sleeve 806. The positioning of the adjustable sleeve 806 may be altered to increase or decrease the side-loading strength of the medical instrument component 800A. To effect the change in side-loading strength, the head of the screw 804 may include multiple notches 810 and the sleeve 806 may correspondingly include multiple protrusions 808. In certain instances, the sleeve 806 may be maintained away from the screw 804, as shown in FIG. 8B. In such instances, the side-loading strength of the non-keyed snap-off screw instrument 800A is equal to the side-loading strength at the breakaway section 816. In other instances, the sleeve 806 may be slid onto the head of the screw 804 such that the protrusions 808 are within the notches 810, as shown in FIG. 8A. This positioning of the sleeve 806 increases the side-loading strength of the medical instrument component 800A as applied side-loads are transferred to the sleeve 806.

In various aspects, the adjustable sleeve 806 may include a hand driver 814. A surgeon may utilize the hand driver 814 to adjust a final torque of the screw 804. For instance, a surgeon may load the snap-off screw instrument including the medical instrument component 800A onto a wire driver and may drive the screw 804 into bone. Once the screw 804 is driven into the bone, the surgeon may remove the wire driver. The surgeon may adjust a final torque of the screw 804 with the sleeve 806 slid onto the head of the screw 804 (e.g., FIG. 8A) via the hand driver 814. After a desired final torque is achieved, the surgeon may slide the sleeve 806 away from the head of the screw 804 and remove the elongated shaft 802 via side loading. The hand driver 814 may be a rectangular prism extending from the sleeve 806 as illustrated. In other instances, the hand driver 814 may have other suitable constructions that enable a surgeon to apply torque to the screw 804, such as a triangular prism, a pentagonal prism, etc.

Figure 8C:
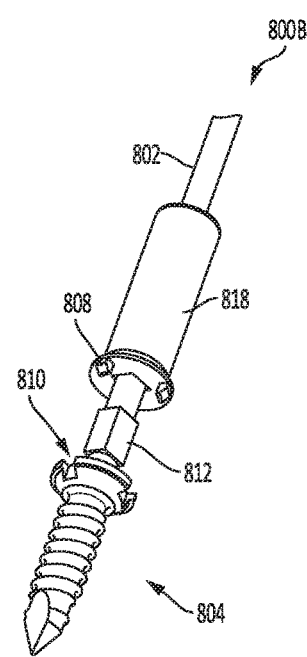
FIG. 8C illustrates a keyed snap-off screw instrument having an adjustable sleeve, according to an aspect of the present disclosure.

FIG. 8C illustrates an example medical instrument component 800B of a keyed snap-off screw instrument. The medical instrument component 800B includes an elongated shaft 802 having a key 812. In such examples, the sleeve 818 is constructed such that its interior matches the key 812 so that the sleeve 818 may be slid over the key 812 and onto the head of the screw 804. The elongated shaft 802 of the medical instrument component 800B includes a breakaway section 816 though it is not illustrated. In such keyed examples, sliding the sleeve 818 onto the head of the screw 804 increases the side-loading strength and the torque strength of the medical instrument component 800B. For example, the interior of the sleeve 818 conforming to the key 812 transfers torque to the sleeve 818. Since the key 812 increases the torque strength of the medical instrument component 800B, the sleeve 818 may be constructed without a hand driver (e.g., hand driver 814) in instances in which the elongated shaft 802 is keyed. Nonetheless, in some instances, the sleeve 818 may also include a hand driver.

Figure 9A:
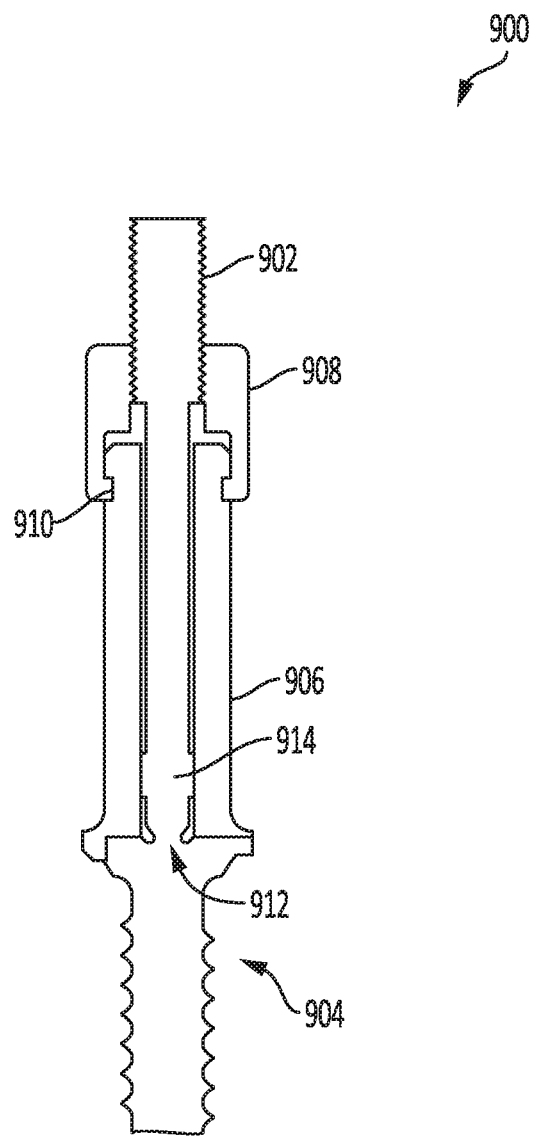
FIGS. 9A and 9B illustrate a cross sectional and perspective view, respectively, of an example medical instrument component with a sleeve adjustment mechanism that includes a nut, according to an aspect of the present disclosure.
Figure 9B:
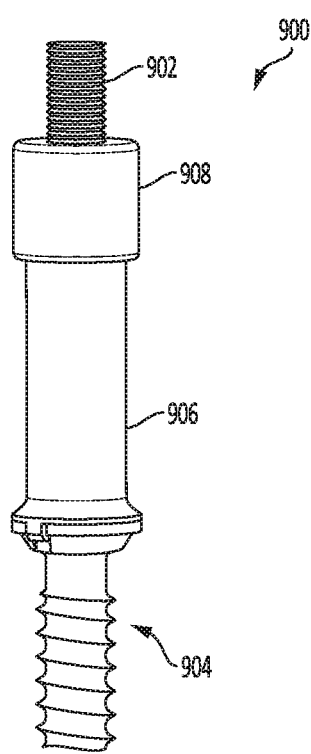

In some examples, the sleeve 806 or 818 may slide freely along the elongated shaft 802. In such examples, a surgeon may need to hold the sleeve 806 or 818 away from the screw 804 when the surgeon does not want the added strength that the sleeve 806 or 818 provides. In other examples, the medical instrument component 800A or 800B may include a sleeve adjustment mechanism that maintains the sleeve in a position on the elongated shaft 802. For example, FIGS. 9A and 9B illustrate a cross sectional and perspective view, respectively, of an example medical instrument component 900 with a sleeve adjustment mechanism that includes a nut 908. The medical instrument component 900 includes an elongated shaft 902 (e.g., a second portion) connected to a screw 904 (e.g., a third portion) at a breakaway section 912 (e.g., a first portion). The elongated shaft 902 includes a key 914 in this example, though in other examples may be constructed without the key 914. The medical instrument component 900 also includes a sleeve 906. The nut 908 couples to the sleeve 906 at the interface 910 such that movement of the nut 908 along the elongated shaft 902 moves the sleeve 906 as well.

Figure 9C:
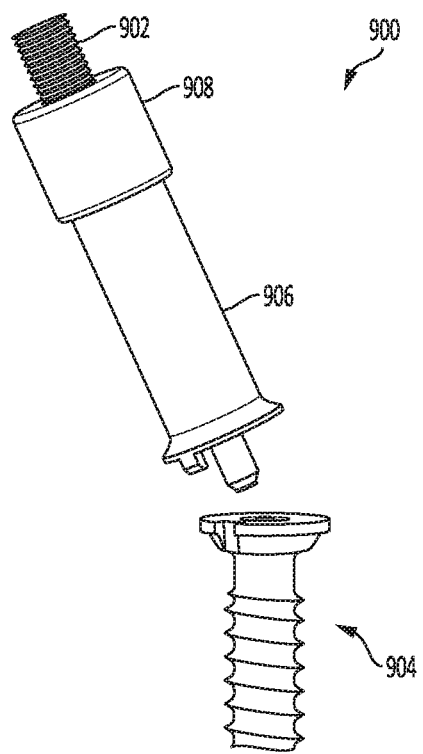
FIG. 9C illustrates a perspective view of the example medical instrument component of FIGS. 9A and 9B after the elongated shaft has broken away from the screw, according to an aspect of the present disclosure.

A portion of the interior of the nut 908 is threaded and engaged with a threaded portion of the elongated shaft 902. As the nut 908 is rotated (e.g., clockwise or counterclockwise), the nut 908 and the sleeve 906 are translated along the elongated shaft 902 towards or away from the screw 904. The engagement of the threads between the elongated shaft 902 and the nut 908 maintains the nut 908 and the sleeve 906 in their respective positions along the elongated shaft when their positioning is not being adjusted. For example, a surgeon may adjust the nut 908 such that the sleeve 906 is positioned away from the screw 904, thereby exposing the breakaway section 912 outside of the sleeve 906. In this positioning, a surgeon may remove the elongated shaft 902 from the screw 904 via side-loading. FIG. 9C illustrates the medical instrument component 900 after the elongated shaft 902 has been broken away from the screw 904.

In some instances, a surgeon may alternatively remove the elongated shaft 902 from the screw 904 by adjusting the positioning of the nut 908 towards the screw 904. Adjusting the positioning of the nut 908 towards the screw 904 applies force to the head of the screw 904 away from the elongated shaft 902. When that force is sufficient to overcome the strength of the breakaway section 912, the screw 904 separates from the elongated shaft 902.

The example sleeve adjustment mechanism described in connection with FIGS. 9A to 9C is merely exemplary. Other suitable adjustment mechanisms may be utilized to maintain a positioning of the sleeve 906. For example, instead of threaded engagement, the nut 908 may be configured to maintain a positioning of the sleeve 906 via friction. In such examples, the nut 908 may include at least one flexible concave shaped portion that applies inward force towards the elongated shaft 902. The inward force is sufficient to maintain a positioning of the nut 908 while also enabling a surgeon to slide the nut 908 along the elongated shaft 902.

Figure 10:
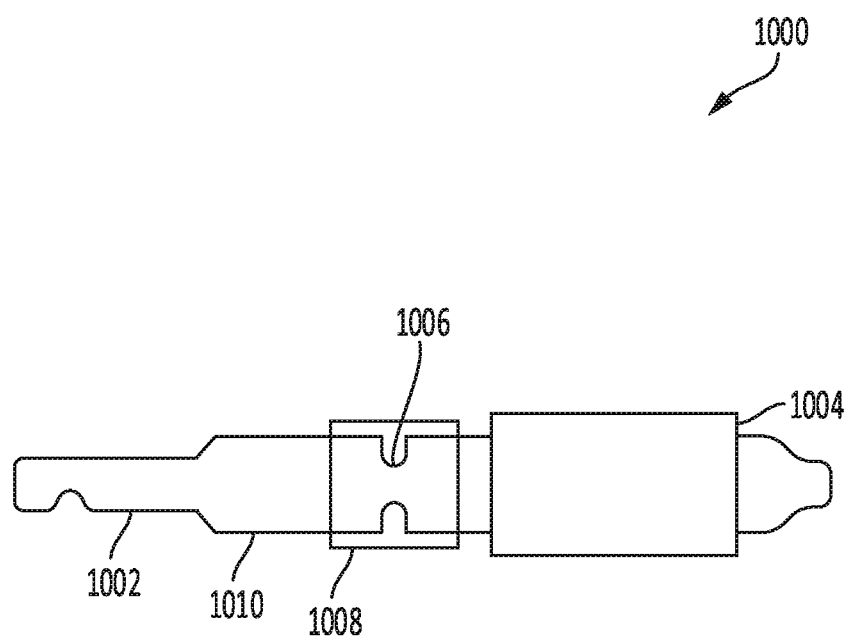
FIG. 10 illustrates a torsional device coupler having a portion with a lowered torsional strength, according to an aspect of the present disclosure.

In some aspects of the present disclosure, the provided medical instrument component may be a coupler that can be added to any torsional device (e.g., a power driver). FIG. 10 illustrates an example torsional device coupler 1000 having a breakaway section with a lowered torsional strength. The torsional device coupler 1000 includes an elongated shaft 1010 having a driver connector 1002. In this example, the driver connector 1002 is an AO connector constructed so that the torsional device coupler 1000 may be attached to a driver. In other examples, the driver connector 1002 may be constructed for attachment to drivers having a different drive feature. The torsional device coupler 1000 also includes a coupler 1004 for attaching the torsional device coupler 1000 to a torsional device. In this example, the coupler 1004 is an AO coupler. In other examples, the coupler 1004 may be constructed for attachment to torsional devices having a different coupling feature.

The elongated shaft 1010 of the torsional device coupler 1000 includes a breakaway section 1006 with a decreased torsional strength as compared to the rest of the elongated shaft 1010. The breakaway section 1006 is illustrated as a continuous decrease in the cross-sectional area of the elongated shaft 1010 (e.g., FIG. 1A). In other examples, the breakaway section 1006 may be constructed as one of the breakaway sections illustrated in FIGS. 1B to 1J, or in another suitable construction that reduces the torque strength of the elongated shaft 1010 to target torsional failure at the breakaway section 1006. In some examples, a series of individual torsional device couplers 1000 may each have a different breakaway torque level so that a surgeon may select an appropriate torsional device coupler 1000 out of the series for a particular procedure. The torsional device coupler 1000 may include a sleeve 1008 to provide additional side-loading strength at the breakaway section 1006, as discussed above with respect to the other example sleeves. It should be appreciated that the sleeve 1008 is illustrated as transparent to illustrate the breakaway section 1006.

In some aspects of the present disclosure, the provided medical instrument component may be a component of an implant, such as a plate, that includes drill/screw guides. Typically, a surgeon positions an implant having guides and then drills a hole into bone through one of the guides. The guide enables the surgeon to quickly drill a hole in the bone that is concentric with the hole in the implant. The guides also enable the surgeon to determine how far into the bone the surgeon drilled. Once the drilling is complete, the surgeon removes the guide so that the surgeon may insert a screw into the drilled hole. Typically, the guides are threadably inserted into the implant so a surgeon must unscrew the guide to remove it, which is cumbersome and time-consuming during the surgical procedure.

Figure 11A:
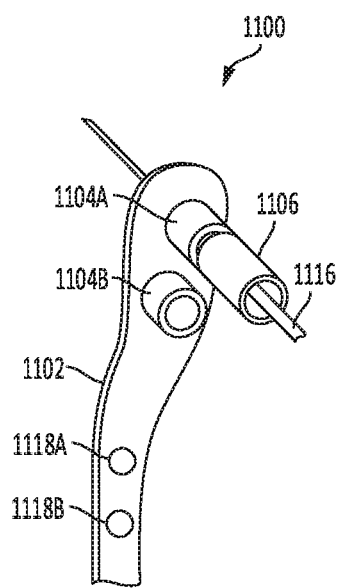
FIGS. 11A and 11B illustrate a plate having snap-off guides, according to an aspect of the present disclosure.
Figure 11B:
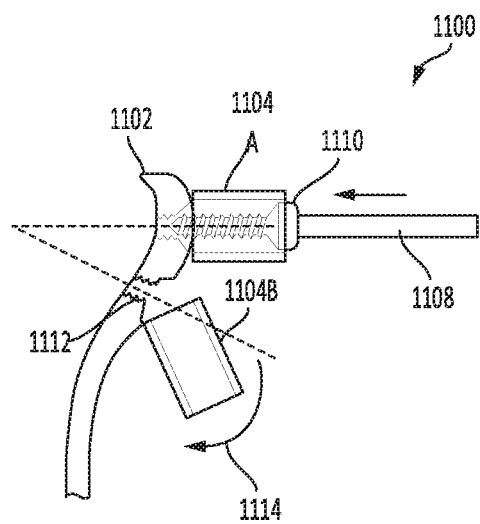

FIGS. 11A and 11B illustrate an example plate 1100 having a body 1102 with a plurality of holes 1118A, 1118B. Each of the holes 1118A, 1118B is associated with a guide 1104A, 1104B. The body 1102 of the plate 1100 may have any suitable shape for an implant. The plate 1100 may have additional holes and/or guides in any suitable orientation on the plate 1100. Typical guides are constructed to concentrically guide a drill bit so that a surgeon may quickly drill a hole in bone that is concentric with the hole in the plate. Each of the guides 1104A, 1104B, however, has a larger diameter than typical guides to also allow passage of a screw head (e.g., the head of the screw 1110). Due to the larger diameter of the guides 1104A, 1104B, in various instances, a drill sleeve 1106 may inserted into a guide 1104A, 1104B. The drill sleeve 1106 effectively reduces the inner diameter (e.g., to an inner diameter equal to typical guides) of the guides 1104A, 1104B and therefore concentrically guides a drill bit (e.g., the drill bit 1116).

A surgeon may therefore drill a hole in a bone through a sleeve 1106 inserted within a guide 1104A, 1104B, remove the sleeve 1106, and then drive (e.g., via a driver 1108) a screw 1110 into the bone hole through the same guide 1104A, 1104B without removing the guide 1104A, 1104B in between. The screw 1110 is inserted through a threaded hole 1112 in the body 1102 of the plate 1100. Only one threaded hole 1112 is indicated for the sake of clarity.

Additionally, the guides 1104A, 1104B of the plate 1100 are attached to the body 1102 such that they may be snapped off. The guides 1104A, 1104B may be snapped off via a side-load or a torsional load. For example, the guides 1104A, 1104B may be tack welded to the body 1102. In other examples, the guides 1104A, 1104B may be machined or three-dimensionally printed as part of the body 1102 such that they may be removed by applying a side-load force or a torsional force. In this way, after a surgeon is done drilling and driving a screw into the bone, the surgeon may quickly remove or "snap off" the guide 1104A, 1104B for that particular threaded hole 1112 of the plate 1100. For example, the surgeon may twist the guide 1104A, 1104B such that it breaks right off as compared to having to twist the guide 1104A, 1104B many revolutions when it is threadably inserted. In such examples, the interface between a guide 1104A, 1104B and the body 1102 designed with reduced torsional strength may be described as a first portion, the body 1102 as a second portion, and the guide 1104A, 1104B as a third portion.

In another example, the surgeon may apply a force in the direction of the arrow 1114 to snap the guide 1104A, 1104B off, as illustrated in FIG. 11B for the guide 1104B. In such examples, the surgeon may apply the force in the direction of the arrow 1114 via the driver 1108 while it is inserted within the guide 1104A, 1104B and after driving the screw 1110.

Accordingly, the example plate 1100 saves a surgeon time during a surgical procedure by enabling a surgeon to simply snap off each guide 1104A, 1104B as the surgeon is finished using it, as compared to the surgeon having to unscrew a typical guide to remove it. Snapping off the guides 1104A, 1104B is also less demanding on a surgeon's fingers as compared to typical guides since the surgeon does not have to unscrew each guide, thus helping maintain the surgeon's dexterity throughout the surgical procedure. Additionally, in some instances, a surgeon may snap off a guide 1104A, 1104B using a tool rather than having to grab it with the surgeon's hands, which can increase the ease of the procedure and save the surgeon time.

Figure 12A:
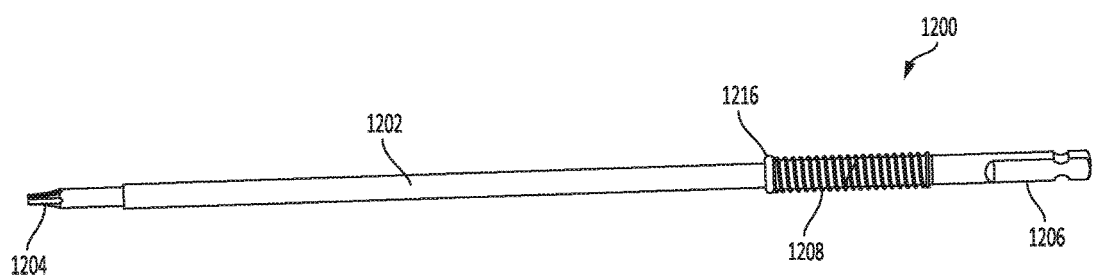
FIG. 12A illustrates a perspective view of an example medical instrument component configured for non-destructive torque relief, according to an aspect of the present disclosure.
Figure 12B:
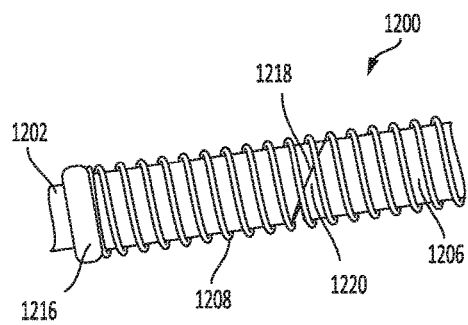
FIG. 12B illustrates a perspective view of a torque relief section of the medical instrument component of FIG. 12A, according to an aspect of the present disclosure.
Figure 12C:
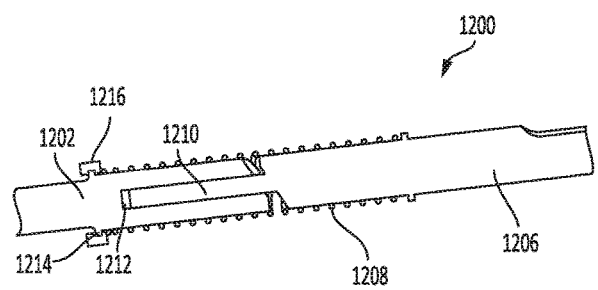
FIG. 12C illustrates a cross sectional view of the torque relief section of the medical instrument component of FIGS. 12A and 12B, according to an aspect of the present disclosure.

The present disclosure additionally provides example medical instrument components for non-destructive torque relief. FIGS. 12A to 12C illustrate an example medical instrument component 1200 configured for non-destructive torque relief. The medical instrument component 1200 includes an elongated shaft 1202. The elongated shaft 1202 includes a drive feature 1204 (e.g., a Phillips drive feature for a screw). The medical instrument component 1200 also includes a driver connector 1206. In this example, the driver connector 1206 is an AO connector constructed so that the medical instrument component 1200 may be attached to a driver. In other examples, the driver connector 1206 may be constructed for attachment to drivers having a different drive feature.

As illustrated, an extension 1210 of the driver connector 1206 is slip fit within the elongated shaft 1202 such that they are concentrically mated. The elongated shaft 1202 includes a slanted surface 1218 that corresponds to a slanted surface 1220 on the driver connector 1206 as illustrated. A spring 1208 surrounds a portion of the elongated shaft 1202 and the driver connector 1206. One end of the spring 1208 is connected to the driver connector 1206. The other end of the spring 1208 is connected to a nut 1216. The nut 1216 is coupled to the elongated shaft 1202 such that it may rotate relative to the elongated shaft 1202. For instance, the nut 1216 may be mated to a protrusion 1214 such that the nut 1216 may rotate relative to the elongated shaft 1202. The spring 1208 is biased to apply a joining force between the elongated shaft 1202 and the driver connector 1206.

As a surgeon utilizes the medical instrument component 1200 to apply torque (e.g., via a driver connected to the driver connector 1206 to drive a screw with the drive feature 1204), the forces between the corresponding slanted surfaces 1218 and 1220, which are increased by the joining force of the spring 1208, work to prevent the elongated shaft 1202 from rotating relative to the driver connector 1206. At a critical torque, however, these forces are overcome and the elongated shaft 1202 rotates relative to the driver connector 1206.

Figure 12D:
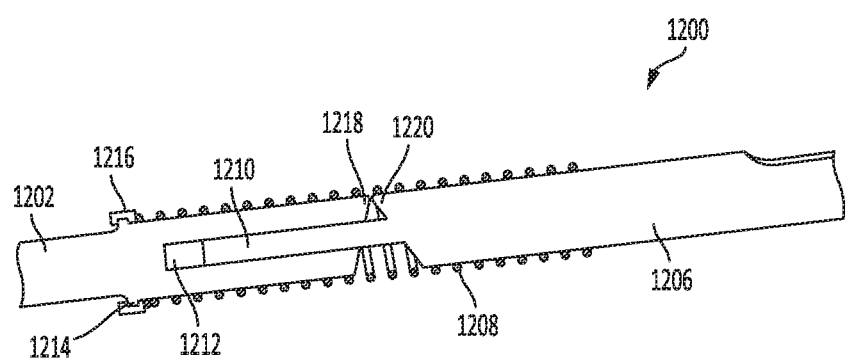
FIG. 12D illustrates a cross sectional view of a critical torque point of the medical instrument component of FIGS. 12A to 12C, according to an aspect of the present disclosure.

The elongated shaft 1202 and the driver connector 1206 rotate relative to one another until the tips of the respective slanted surfaces 1218 and 1220 contact one another as illustrated in FIG. 12D. Increasing torque may be applied until this point, as the slanted surface 1220 "travels up" the slanted surface 1218 and the driver connector 1206 separates from the elongated shaft 1202. The extension 1210 maintains axial alignment of the elongated shaft 1202 and the driver connector 1206 as they separate from one another. After this point, however, further rotation or torque results in the slanted surface 1220 "traveling down" the slanted surface 1218 and the amount of torque that can be applied by the medical instrument component 1200 decreases. In this way, the medical instrument component 1200 limits the amount of torque that a surgeon can apply and provides non-destructive torque relief The level of torque that a surgeon may apply with the medical instrument component 1200 may depend upon the slanted surfaces 1218 and 1220 and the strength of the spring 1208. For instance, a greater slope in the slanted surfaces generates a greater counteracting force and thus enables a surgeon to apply a greater amount of torque. A greater strength of the spring 1208 creates a stronger joining force between the driver connector 1206 and the elongated shaft 1202 that helps prevent the slanted surface 1220 from "traveling up" the slanted surface 1218. A greater strength of the spring 1208 therefore enables a surgeon to apply a greater amount of torque.

Figure 13A:
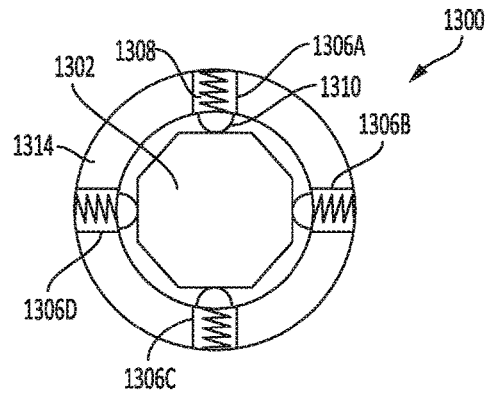
FIGS. 13A and 13B illustrate a cross section and schematic, respectively, of an example non-destructive torque relief medical instrument including a medical instrument component having a ring with spring and ball plungers positioned around a shaft, according to an aspect of the present disclosure.

In another aspect of the present disclosure, a medical instrument component for non-destructive torque relief includes one or more spring and ball plungers. A shaft having at least one flat surface may be inserted within the medical instrument component such that the at least one flat surface contacts the spring and ball plunger(s). FIG. 13A illustrates a cross section of a medical instrument 1300 including a medical instrument component 1314 having spring and ball plungers 1306A, 1306B, 1306C, 1306D positioned around a shaft 1302. In the illustrated embodiment, the shaft 1302 has an octagonal cross section. In other embodiments, the shaft 1302 may be constructed having other suitable cross sectional shapes having at least one flat surface (e.g., pentagonal, hexagonal, heptagonal, circular aside from one flat surface, etc.). The end of the shaft 1302 not inserted within the medical instrument component 1314 may include a drive feature.

Each spring and ball plunger 1306A, 1306B, 1306C, and 1306D includes a spring 1308 connected to a ball 1310, though only those of spring and ball plunger 1306A are indicated for the sake of clarity. The spring and ball plungers 1306A, 1306B, 1306C, 1306D are constructed such that the springs 1308 are biased to apply a compressive force to a flat surface of the shaft 1302 via the balls 1310 connected to the springs 1308. The flat surface of the shaft 1302 enables a greater contact surface between the shaft 1302 and the balls 1310 to enable greater compressive force. In some examples, such as the illustrated example in FIG. 13A, the spring and ball plungers 1306A, 1306B, 1306C, and 1306D are individually integrated with the medical instrument component 1314. In other examples, the spring and ball plungers 1306A, 1306B, 1306C, and 1306D may be connected as part of a ring (e.g., FIG. 13B). The ring may be a separate component that is connected to the medical instrument component 1314 or may be integrated with the medical instrument component 1314.

Torque may be generated between the spring and ball plungers 1306A, 1306B, 1306C, and 1306D and the shaft 1302, for example, when a surgeon rotates the medical instrument component 1314 to drive a screw via a drive feature of the shaft 1302. As such torque is generated, friction between the balls 1310 and the shaft 1302 due to the compressive force applied by the springs 1308 initially prevents the medical instrument component 1314 from rotating relative to the shaft 1302. Once a critical level of torque is reached, however, the frictional forces are overcome and the medical instrument component 1314 "slips" or rotates relative to the shaft 1302.

In various examples, the critical level of torque may be tailored based on one or more parameters, such as a quantity of flat surfaces on the shaft 1302, a size of the flat surfaces, a quantity of spring and ball plungers 1306A, 1306B, 1306C, 1306D, and a strength of the springs 1308. For instance, a medical instrument component 1314 having a greater quantity of spring and ball plungers 1306A, 1306B, 1306C, 1306D may provide a greater critical torque level because each additional spring and ball plunger 1306A, 1306B, 1306C, 1306D creates additional frictional force, which requires a greater critical torque level to overcome. Similarly, stronger springs 1308 on the spring and ball plungers 1306A, 1306B, 1306C, 1306D creates additional friction force. A person having skill in the art will appreciate the various combinations that may be made and how they respectively affect the critical torque level.

Figure 13B:
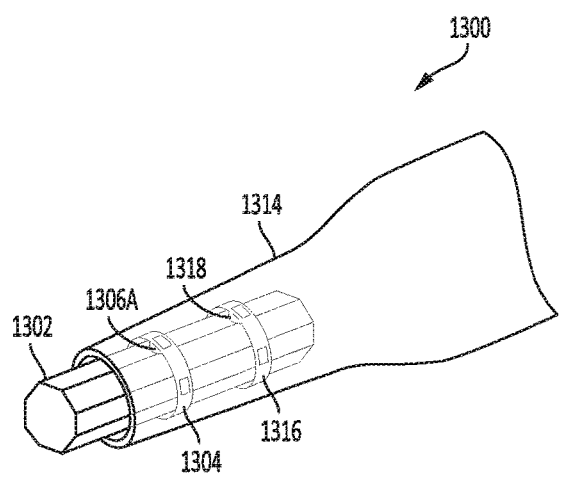

FIG. 13B illustrates a perspective view of the example medical instrument 1300 in which the spring and ball plungers are connected as part of a ring. The medical instrument component 1314 includes two separate rings 1304 and 1316. Each ring 1304 and 1316 includes multiple spring and ball plungers 1306A and 1318, respectively. In some examples, the medical instrument component 1314 may be constructed to include a handle for a surgeon to hold when driving in a screw with the medical instrument 1300. In other examples, the medical instrument component 1314 may be constructed as a coupler that may be connected to a driving device, such as a power driver. In any of such examples, as a surgeon drives a screw with the medical instrument 1300, the frictional forces between the balls of the spring and ball plungers 1306A and 1318 and the shaft 1302 prevents the medical instrument component 1314 from rotating relative to the shaft 1302, which enables the surgeon to apply torque to the screw. Once the surgeon applies a critical level of torque, the medical instrument component 1314 "slips" or rotates relative to the shaft 1302. An amount of torque above the critical level cannot be applied since it causes the medical instrument component 1314 to "slip" or rotate. In this way, the medical instrument component 1314 limits the amount of torque that the surgeon can apply to help prevent damage to an implant or bone.

Figure 14A:
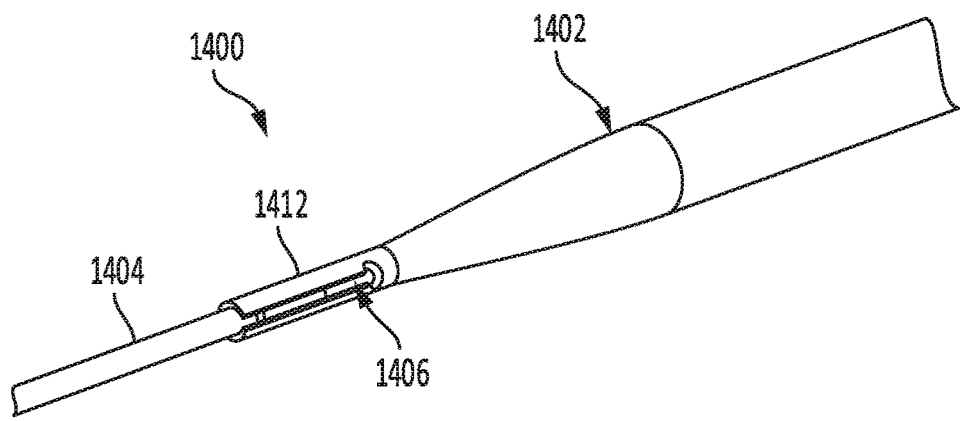
FIGS. 14A to 14C illustrate a medical instrument for non-destructive torque relief including an elastically deformable medical instrument component having a relief slot, according to an aspect of the present disclosure.
Figure 14B:
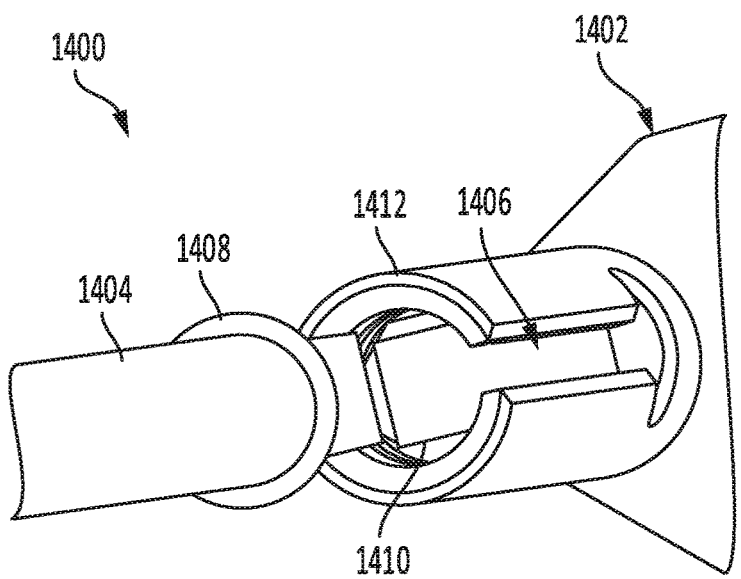
Figure 14C:
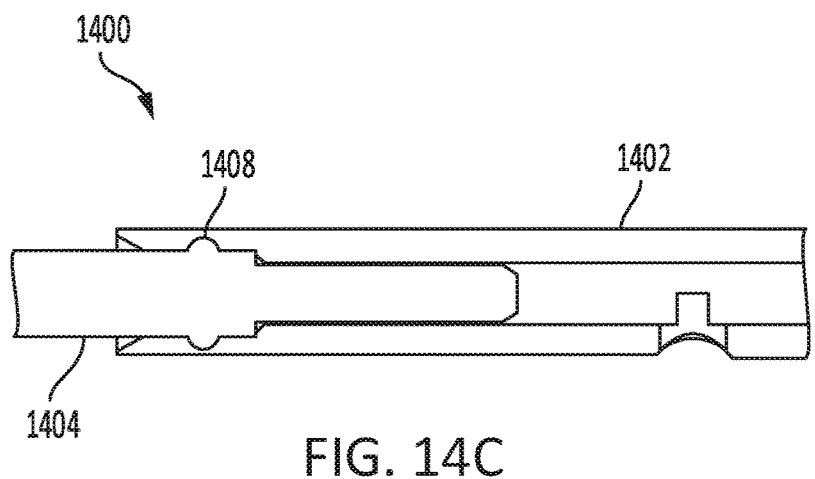

In another aspect of the present disclosure, a medical instrument for non-destructive torque relief includes an elastically deformable medical instrument component having a relief slot. FIGS. 14A to 14C illustrate an example medical instrument 1400 including a medical instrument component 1402 and a shaft 1404 with one of its ends positioned within an insertion end 1412 of the medical instrument component 1402. The other end of the shaft 1404 may include a drive feature. In the illustrated example, the medical instrument component 1402 is configured as a handle. In other examples, the medical instrument component 1402 may be configured as a coupler. The medical instrument component 1402 is constructed of an elastically deformable material that is also sufficiently rigid to be used to apply torque (e.g., PEEK, polyetherimide (Ultem®), polyoxymethylene (Delrin®)). The medical instrument component 1402 includes at least one relief slot 1406. A relief slot 1406 may be a cut-out portion of material that enables the elastically deformable medical instrument component 1402 to deform by expanding the relief slot 1406, such as that illustrated in FIGS. 14A and 14B.

The interior of the insertion end 1412 of the medical instrument component 1402 includes at least one flat surface. For example, the insertion end 1412 is illustrated in FIG. 14B as having five flat surfaces (e.g., the fourth side of the square cross section is split into two by the relief slot 1406). The end of the shaft 1404 inserted into the insertion end 1412 includes one or more flat surfaces that line up with the at least one flat surface of the insertion end 1412. For example, the shaft 1404 is illustrated in FIG. 14B as having a square cross section that lines up with the cross section of the insertion end 1412. The interfacing of the flat surfaces helps prevent the medical instrument component 1402 from rotating relative to the shaft 1404 up to a critical level of torque.

For example, as a surgeon drives a screw with the medical instrument 1400, the forces between the flat surfaces of the insertion end 1412 and the shaft 1404 prevents the medical instrument component 1402 from rotating relative to the shaft 1404, which enables the surgeon to apply torque to the screw. Increasing torque, however, also cause the relief slot 1406 to expand since the medical instrument component 1402 is elastically deformable. As the relief slot 1406 expands, the diameter of the insertion end 1412 increases and contact decreases between the flat surfaces of the insertion end 1412 and the flat surfaces of the shaft 1404. Once the surgeon applies a critical level of torque, the contact between flat surfaces decreases to a point at which the medical instrument component 1402 "slips" or rotates relative to the shaft 1404. An amount of torque above the critical level cannot be applied since it causes the medical instrument component 1402 to "slip" or rotate. In this way, the medical instrument 1400 limits the amount of torque that the surgeon can apply to help prevent damage to an implant or bone.

The interior of the insertion end 1412 of the medical instrument component 1402 may also include a notch. The insertion end 1412 and the shaft 1404 may be snapped together such that the protrusion 1408 of the shaft 1404 is positioned within the notch, as shown in FIG. 14C. For example, as the shaft 1404 is inserted or slid into the insertion end 1412, the protrusion 1408 causes the elastically deformable insertion end 1412 to expand. Once the protrusion 1408 reaches the notch, the insertion end 1412 returns to its resting shape. The protrusion 1408 positioned within the notch helps maintain axial alignment between the medical instrument component 1402 and the shaft 1404 without impacting torsional strength.

As used herein and in the appended claims, the singular form of a word includes the plural, unless the context clearly dictates otherwise. Thus, the references "a," "an" and "the" are generally inclusive of the plurals of the respective terms. For example, reference to "a ring" includes a plurality of such "rings." The term "and/or" used in the context of "X and/or Y" should be interpreted as "X," or "Y," or "X and Y."

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A medical instrument component comprising:
an elongated shaft including a first portion, a second portion, and a third portion, wherein the first portion is between the second and third portions; and
a sleeve configured to be positioned at least some of the time around the first portion, wherein the sleeve is connected to the second portion or the third portion,
wherein the first portion is configured to have a lower torsional strength than the second and third portions such that the first portion experiences torsional failure at a lower torque force than the second or third portions,
wherein the sleeve is configured to be positioned around the first portion so that the sleeve covers the first portion, at least a proximal portion of the second portion, and at least a distal portion of the third portion, thereby reducing side-loading stress in the first portion,
wherein the second portion of the elongated shaft comprises a notch, wherein at least a portion of the notch overlaps with the sleeve, wherein the notch of the second portion is configured to receive a driver.

2. The medical instrument component of claim 1, wherein a cross sectional area of the first portion continuously decreases from a cross sectional area at an interface with the second portion to a minimum cross sectional area, and from a cross sectional area at an interface with the third portion to the minimum cross sectional area.

3. The medical instrument component of claim 2, wherein the cross sectional area of the first portion linearly decreases.

4. The medical instrument component of claim 1, wherein the first portion includes a plurality of separate indentations towards a central axis of the elongated shaft.

5. The medical instrument component of claim 4, wherein the plurality of separate indentations include a flat surface.

6. The medical instrument component of claim 1, wherein the first portion includes a continuous spiral indentation.

7. The medical instrument component of claim 1, wherein the first portion includes a first indentation and a plurality of second indentations that are indented greater than the first indentation.

8. The medical instrument component of claim 1, wherein the first portion includes at least one opening through the elongated shaft.

9. The medical instrument component of claim 8, wherein the opening is larger on one end as compared to its opposite end.

10. The medical instrument component of claim 8, wherein a positioning of the sleeve is adjustable along the opening of the first portion such that the torsional strength of the first portion is adjustable based on the positioning of the sleeve.

11. The medical instrument component of claim 1, wherein a positioning of the sleeve is fixed relative to the elongated shaft.

12. The medical instrument component of claim 1, wherein a positioning of the sleeve is adjustable relative to the elongated shaft.

13. The medical instrument component of claim 12, wherein the positioning of the sleeve is adjustable via threaded engagement with the elongated shaft.

14. The medical instrument component of claim 1, wherein the third portion of the elongated shaft includes a drive feature.

15. The medical instrument component of claim 14, wherein the first portion and the second portion are configured such that, subsequent to torsional failure resulting in breakage, the second portion and a remaining portion of the first portion are configured as the drive feature.

16. The medical instrument component of claim 1, wherein the torsional failure experienced by the first portion includes the first portion breaking into two separate components.

17. The medical instrument component of claim 1, wherein the medical instrument component is a component of a reamer or a drill.

18. The medical instrument component of claim 1, wherein the second or third portion of the elongated shaft is configured to removably couple with a driver.

19. The medical instrument component of claim 1, wherein the third portion is a screw and the second portion includes a key.

20. The medical instrument component of claim 1, wherein the third portion is a screw and the sleeve includes a hand driver.

* * * * *